US00PP24014P3

(12) United States Plant Patent
Ranney

(10) Patent No.: US PP24,014 P3
(45) Date of Patent: Nov. 5, 2013

(54) ***CALYCANTHUS* PLANT NAMED 'APHRODITE'**

(50) Latin Name: ***Calycanthus chinensis*×*Calycanthus occidentalis***
Varietal Denomination: Aphrodite

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 113 days.

(21) Appl. No.: 13/317,289

(22) Filed: Oct. 13, 2011

(65) Prior Publication Data

US 2013/0055477 P1 Feb. 28, 2013

(30) Foreign Application Priority Data

Aug. 25, 2011 (CA) ..... PBR 11-7360

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu

(74) *Attorney, Agent, or Firm* — Michael Best & Friedrich LLP

(57) ABSTRACT

*Calycanthus* 'Aphrodite' is a medium-sized, multi-stemmed shrub with glossy foliage. The large, purple-red, magnolia-like flowers have yellow tips on the inner tepals and a light fruity fragrance. The flowers are produced on long pedicles/peduncles at the distal end of the current year's growth for 6-8 weeks in late spring and early summer.

3 Drawing Sheets

Genus and species:
*Calycanthus chinensis*×*Calycanthus occidentalis.*
Variety denomination: 'Aphrodite'.
This application claims the benefit of Canadian Serial No. 11-7360 filed 25 Aug. 2011.

BACKGROUND OF THE INVENTION

*Calycanthus* are deciduous flowering shrubs of the genus Calycanthaceae. *Calycanthus floridus* (also commonly referred to as the sweetshrub) is perhaps the most well known member of the genus, and is sometimes grown as an ornamental landscape plant, particularly in parts of the Eastern United States. Plant height can vary and ranges from 1 to 2.5 meters, growing as multi-stemmed shrubs. The flowers range in size (2-3 cm across) with tepals that vary from reddish purple to a dark chocolate brown. The fragrance is variable, but can have a pleasant fruity aroma.

Applicants believe there are additional opportunities for new and distinct *Calycanthus* as a landscape plant, e.g., for borders, foundations or naturalizing.

SUMMARY OF THE INVENTION

The present invention comprises a new and distinct variety of *Calycanthus,* botanically known as *Calycanthus* L. 'Aphrodite', and hereinafter referred to by the varietal name 'Aphrodite'. This new *Calycanthus* was developed through a breeding program at Mills River, N.C. 'Aphrodite' is an $F_1$ hybrid between *Calycanthus chinensis* and *Calycanthus occidentalis.* The first asexual propagation of 'Aphrodite' was carried out in June 2005 by rooting stem cuttings at the North Carolina State University, Mountain Horticultural Crops Research Station, Mills River, N.C. and has been asexually reproduced repeatedly by vegetative cuttings in North Carolina over a six year period.

'Aphrodite' roots readily from firm, terminal and subterminal, softwood cuttings treated with a basal dip of 5000 to 10,000 ppm indole butyric acid (potassium salt) in water. 'Aphrodite' has been found to retain its distinctive characteristics through successive asexual propagations.

'Aphrodite', when grown under normal horticultural practices at Mills River, N.C., exhibited a number of distinguishing characteristics, including at least one of the following:

1. Large, purple-red, magnolia-like flowers with yellow apical margins on inner tepals.
2. Terminal and subterminal (axillary) flowers blooming over an eight week period providing a long bloom season.
3. Increased floral visibility due to flowers being held on stalks (pedicels and peduncles) above the foliage.
4. Lightly fragrant flowers with a fruity aroma.
5. Attractive glossy foliage.

BRIEF DESCRIPTION OF THE PHOTOGRAPHS

This new *Calycanthus* plant is illustrated by the accompanying photographs which show the plant's form, foliage and flowers. The colors shown are as true as can be reasonably obtained by conventional photographic procedures. The photographs were taken in June 2011 of nine-year-old plants, growing under field conditions in Mills River, N.C.

Figure 1:
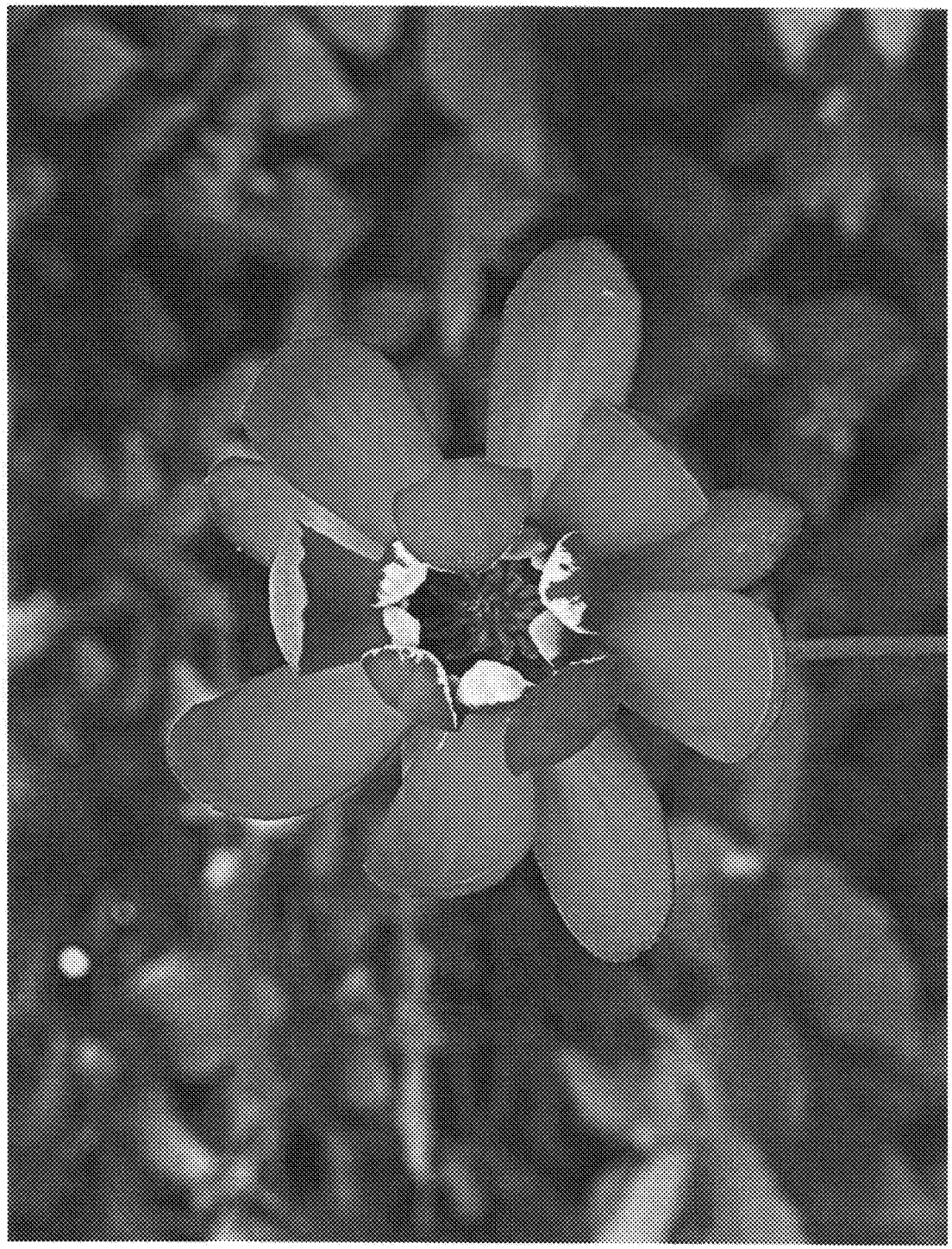
Figure 2:
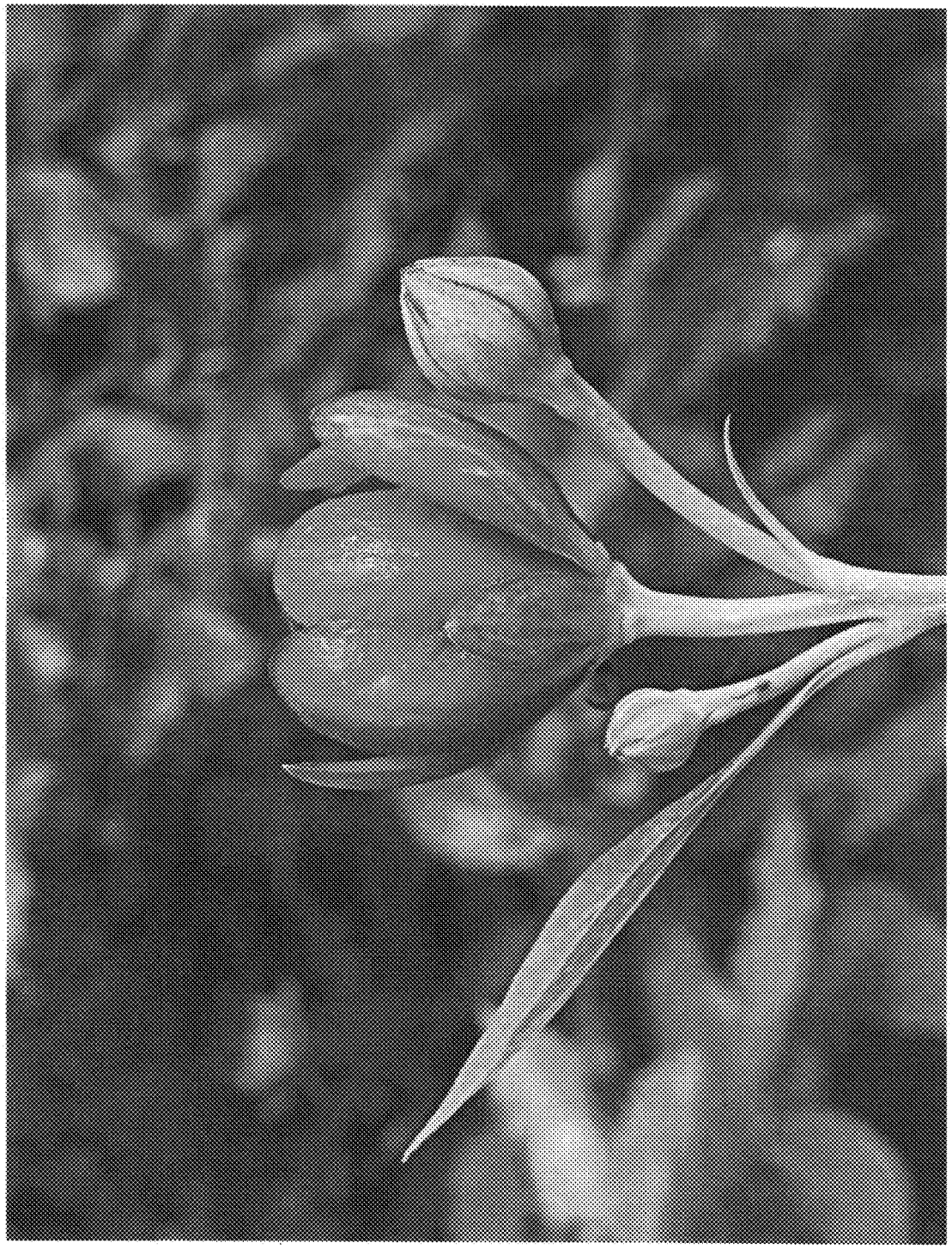
Figure 3:
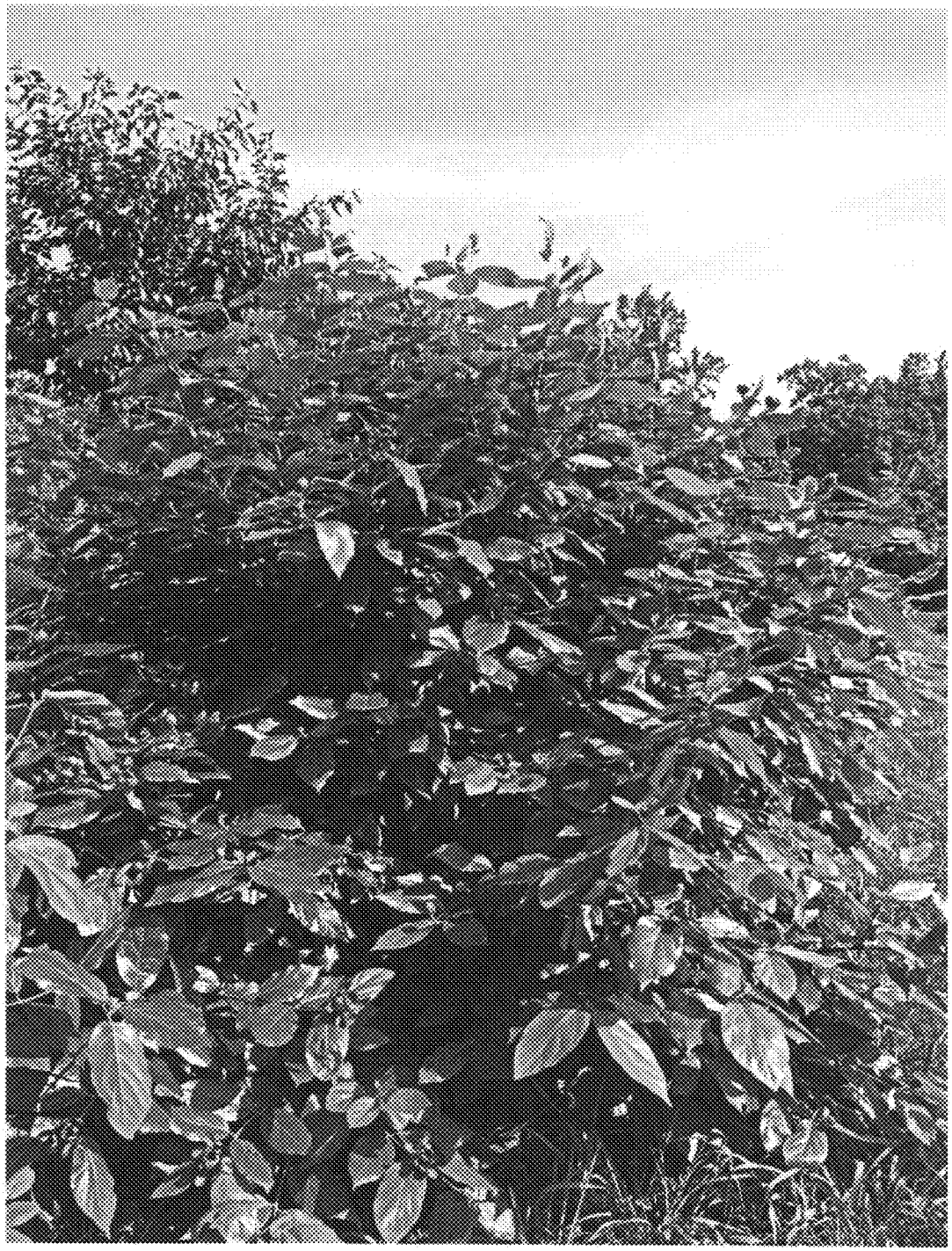

FIG. 1 shows a typical flower.
FIG. 2 shows the sub-terminal, axillary flowers.
FIG. 3 shows the entire plant.

DETAILED BOTANICAL DESCRIPTION

The following detailed description sets forth the distinctive characteristics of 'Aphrodite'. The detailed description was taken on nine-year-old plants growing under field conditions in Mills River, N.C. in April 2008. Color references are to The R.H.S. Colour Chart of The Royal Horticultural Society of London (R.H.S.), 2001 Edition.

Classification: Shrub.

Botanical name: *Calycanthus* L. 'Aphrodite'.

Common name: Sweetshrub.

Parentage: *Calycanthus chinensis*×*Calycanthus occidentalis*.

Plant description:

*Growth habit.*—Multistemmed shrub.

*Plant shape.*—Globose.

*Height at maturity.*—3-4 meters.

*Width at maturity.*—3-4 meters.

*Vigor.*—Vigorous, shoots growing up to 0.5 meter in a season.

Stem:

*Immature stem texture.*—Glabrous to tomentulose.

*Immature stem color.*—RHS 144A (Yellow-Green).

*Mature stem texture.*—Rugulose, glaborous.

*Mature stem color.*—Closest to RHS 199A (Greyed-Brown).

Trunk: Typical diameter of nine-year-old plant 2 cm above the soil: 18.6 to 36.1 mm.

Branches:

*Length.*—15 to 200 cm.

*Diameter.*—5.5 to 13.6 mm.

Foliage:

*Type.*—Deciduous.

*Arrangement.*—Opposite.

*Shape.*—Elliptical.

*Apex.*—Acuminate to obtuse.

*Veins.*—Type: Pinnate. Adaxial & abaxial vein color: Closest to RHS 148C (Yellow-Green). Surface texture: Glabrous to tomentulose.

*Base.*—Rounded to attenuate.

*Margin.*—Entire.

*Mature leaf size.*—Length: Average is 14.2 cm (range is 12.0 to 17.0 cm). Width at widest: Average is 6.8 cm (range is 5.3 to 7.5 cm).

*Immature leaf color.*—Adaxial (upper) surface: Glossy, RHS 144A (Yellow-Green). Abaxial (lower) surface: Glaucesant Closest to RHS 144A (Yellow-Green).

*Immature leaf texture.*—Adaxial surface: Scabridulous. Abaxial surface: Interveinal areas glabrous with veins tomentulose.

*Mature leaf color.*—Adaxial (upper) surface: Glossy, Closest to RHS 137A (Green). Abaxial (lower) surface: Glaucesant, RHS 137B (Green). Mature Leaf Texture: Adaxial: Scabridulous. Abaxial: Interveinal areas glabrous, veins tomentulose.

*Fall foliage color.*—Yellow (20A) to golden brown (22A).

*Leaf attachment.*—Petiolate.

*Petiole.*—Shape: Laterally compressed cylinder with an adaxial groove. Length: Average is 10.8 mm (range is 7.86 to 14.96 mm). Width: Average is 2.2 mm (range is 1.71 to 2.61 mm).

*Surface.*—Tomentulose to glabrous.

Inflorescence: *Calycanthus* 'Aphrodite' produces complete flowers on shoot terminals and frequently on subtending axils. Flowers have 26 to 30 tepals in a whorled series. Flowers are held on 16.6 to 26.5 mm stalks (pedicels and peduncles) at the distal end of the current season's growth. These flowers are magnolia-like and open with the greyed-orange apical margin of the inner tepals displayed prominently.

Flowering season: In Mills River, N.C. flowering begins in early May and continues through June and sporadically in July.

Lastingness of flower on the plant: 2 to 4 days.

Fragrance: Light fruity or melon-like fragrance.

Self cleaning or persistent: Self Cleaning.

Bud:

*Bud shape.*—Orbicular.

*Bud diameter at balloon stage.*—Average 19.61 mm (range is 15.42 to 21.89 mm).

*Bud length at balloon stage.*—Average 22.65 mm (range is 15.42 to 26.55 mm).

*Bud color.*—Margins of tepals RHS N186C (Greyed-Purple) with interior color of tepals and dominate color of bud RHS 183B to 183C (Greyed-Purple).

Perianth:

*Diameter at anthesis.*—Average 84.83 mm (range is 78.43 to 92.48 mm).

Tepal:

*Number of tepals per flower.*—9 to 13 inner tepals, 16 to 20 outer tepals. Average 27 (range is 26 to 30).

*Outer tepal color, adaxial (upper) surface at anthesis.*—Tepal margin RHS 59A (Red-Purple) with interior flushed with RHS 186A (Greyed-Purple).

*Outer tepal color, abaxial (lower) surfaces at anthesis.*—RHS 59A (Red-Purple).

*Inner tepal color, adaxial surface.*—RHS 59A (Red-Purple) with apical margin of tepal RHS 163D (Greyed-Orange).

*Inner tepal color, abaxial surface.*—RHS 59A (Red-Purple).

*Surface texture and appearance for both adaxial and abaxial surfaces.*—Puberulous: fine hairs at right angles to the tepal surface, although tepal has texture and appearance of filamentous silk cloth.

*Shape.*—Obovate.

*Apex.*—Obtuse.

*Base.*—Cuneate.

*Margin.*—Entire.

*Outer tepal.*—Length: Average is 38.84 mm (range is 36.77 to 40.33 mm). Width: Average is 17.19 mm (range is 16.49 to 18.14 mm).

*Inner tepal.*—Length: Average is 18.45 mm (range is 17.85 to 19.29 mm). Width: Average is 8.94 mm (range is 8.55 to 9.62 mm).

*Tepals, fused or unfused.*—Unfused.

Pedicel/peduncle:

*Color.*—RHS 144A (Yellow-Green).

*Length.*—Average 20.89 mm (range is 16.58 to 26.48 mm).

*Width.*—Average 3.25 mm (range is 2.37 to 3.73 mm).

*Shape.*—Cylindrical.

*Surface texture.*—Tomentulose.

Bract:

*Number.*—3.

*Length.*—Average 8.21 mm (range is 6.95 to 9.52 mm).

*Width.*—Average 2.62 mm (range is 2.08 to 3.11 mm).

*Color.*—RHS N144A (Yellow-Green) on both upper and lower surface.

*Shape.*—Lanceolate.

*Apex.*—Acuminate.

*Base.*—Truncate.

*Surface texture.*—Glabrous to tomentulose on both upper and lower surface.

Reproductive organs:

*Stamen.*—Quantity per flower: Average 21 (range is 19 to 23). Shape: Linear to lanceolate. Anthers are longitudinally adnate to stalkly filament. Occassional petaloid stamens occur. Color at anthesis: RHS 10A (Yellow) and RHS 183A (Greyed-Purple) maturing to RHS 10A (Yellow) spotting with RHS 183A (Greyed-Purple) and RHS 10B (Yellow). Filament Length: Average is 1.9 mm (range is 1.3 to 2.2 mm). Width of filament: Average 1.0 mm (range is 0.08 to 1.4 mm).

*Anther.*—Length: Average is 5.63 mm (range is 5.00 mm to 7.00 mm). Width at widest: Average is 1.2 mm (range is 1.1 to 1.5 mm). Dehiscence: Longitudinally. Anther Color: closest to RHS 186A (Greyed-Purple). Pollen color: RHS 10B (Yellow). Attachment: Longitudinally adnate to filament.

*Pistil.*—Style Length: Average 7.25 mm (range 7.00 to 8.00 mm). Style Width at midpoint: Filamentitious less than 0.5 mm. Style Color: Translucent white RHS N155. Stigma Color: Translucent white RHS N155. Ovary diameter: Average 13.6 mm (range 12.00 to 19.00 mm). Number of Pistils per Flower: Approximately 15.

*Fruit/seed set.*—Fruit: Not currently available.

Disease and insect resistance: Cultural requirements, disease and pest resistance/susceptibility for *Calycanthus* 'Aphrodite' appear to be similar to other *Calycanthus.* This variety can be grown in full sun to shade with best growth on moist sites that do not become overly dry. *Calycanthus* 'Aphrodite' tolerates a range of soil pH from about 4.5 to 6.5. The plant hardiness zone is USDA Zone 6-10.

Comparison with parental lines and known cultivars: 'Aphrodite' has primarily purple-red tepals, an imbricate tepal arrangement, and a light fruity fragrance while the female parent, *C. chinensis,* has a two-series tepal arrangement with the whitish-pink outer tepals and yellow inner tepals and no fragrance.

'Aphrodite' has large flowers, 78-93 mm in diameter with inner tepals having a yellow distal margin while the male parent, *C. occidentalis,* has smaller flowers, 20-40 mm in diameter, with reddish-brown tepals.

Table 1 shows the differences between 'Aphrodite', *Calycanthus* 'Venus' U.S. Plant Pat. No. 15,925 and *Calycanthus* 'Hartlage Wine' (unpatented).

TABLE 1

COMPARISON TO COMMERCIAL CULTIVARS

| | Cultivar | | |
|---|---|---|---|
| Trait | 'Aphrodite' | 'Venus' | 'Hartlage Wine' |
| Diameter of Flower | 7.8 to 9.3 cm | 7.5 to 11.5 cm | 6.9 to 8.5 cm |
| Color of Flower | Outer Tepals: margin RHS 59A (Red-Purple) with interior flushed with RHS 186A (Greyed-Purple) Inner Tepals: RHS 59A (Red-Purple) with apical margin of tepals RHS 163D (Greyed-Orange) | Outer Tepals: RHS 155A (White) Inner Tepals: RHS 155A (White) with apical margin RHS 5C (yellow) with blush of RHS 60C (Red-Purple) on edge and base | Outer Tepals: Margins RHS 187B (Greyed-Purple) with interior RHS 53A (Red) Inner Tepals: RHS 187B (Greyed-Purple) with apical margins RHS 163C (Yellow) |
| Flower Fragrance | Light fruity | Fruity | No Fragrance |
| Tepal Presentation | Open flower with yellow apical margin of inner tepals prominently displayed | Outer tepals opening fully to display the yellow and red inner whorl on some flowers while outer tepals partially obscures inner tepals on other flowers | Outer tepals cup to partial obscure creamy white to yellow apical margins of inner tepals. |
| Bud Color | Margins of tepals RHS N186C (Greyed-Purple) with interior color of tepals and dominate color of bud RHS 183B to 183C (Greyed-Purple) | Outer tepals are primarily RHS 1D (green-yellow) with some ranging from RHS 144C to RHS 144D (Yellow-Green) | Margins of tepals closest to RHS N186 (Greyed-Purple) with interior color of tepals and dominate color of bud RHS 187B (Greyed-Purple) |

I claim:

1. A new and distinct variety of *Calycanthus* plant as shown and described herein.

* * * * *